(12) United States Patent
Chovanda et al.

(10) Patent No.: US 9,826,925 B2
(45) Date of Patent: Nov. 28, 2017

(54) ANALYTE METER WITH BASIC AND ADVANCED METER PRESET MODE SELECTION BASED ON STRUCTURED QUERIES

(71) Applicant: LifeScan, Inc., Milpitas, CA (US)

(72) Inventors: Sweta Chovanda, Exton, PA (US); Shawn Berven, Philadelphia, PA (US)

(73) Assignee: LifeScan, Inc., Wayne, PA (US)

( * ) Notice: Subject to any disclaimer, the term of this patent is extended or adjusted under 35 U.S.C. 154(b) by 0 days.

(21) Appl. No.: 13/689,446

(22) Filed: Nov. 29, 2012

(65) Prior Publication Data

US 2014/0148668 A1    May 29, 2014

(51) Int. Cl.
A61B 5/145    (2006.01)
A61B 5/00    (2006.01)

(52) U.S. Cl.
CPC .......... *A61B 5/14532* (2013.01); *A61B 5/743* (2013.01)

(58) Field of Classification Search
CPC ..................... A61B 5/743; A61B 5/14532
See application file for complete search history.

(56) References Cited

U.S. PATENT DOCUMENTS

| | | | |
|---|---|---|---|
| 7,912,655 B2 | 3/2011 | Power et al. | |
| 2009/0150186 A1* | 6/2009 | Cohen ................ | G06F 19/3406 705/3 |
| 2010/0041084 A1 | 2/2010 | Stephens et al. | |
| 2010/0331650 A1* | 12/2010 | Batman et al. ............... | 600/365 |
| 2011/0205064 A1 | 8/2011 | Strachan et al. | |

* cited by examiner

*Primary Examiner* — Sam P Siefke (57) ABSTRACT

Described are methods and systems to allow users to select a basic mode or an advanced mode in which additional features can be customized for the user based on structured queries presented to the user.

5 Claims, 6 Drawing Sheets

ANALYTE METER WITH BASIC AND ADVANCED METER PRESET MODE SELECTION BASED ON STRUCTURED QUERIES

BACKGROUND

Analyte detection in physiological fluids, e.g. blood or blood derived products, is of ever increasing importance to today's society. Analyte detection assays find use in a variety of applications, including clinical laboratory testing, home testing, etc., where the results of such testing play a prominent role in diagnosis and management in a variety of disease conditions. Analytes of interest include glucose for diabetes management, cholesterol, and the like. In response to this growing importance of analyte detection, a variety of analyte detection protocols and devices for both clinical and home use have been developed.

One type of method that is employed for analyte detection is an electrochemical method. In such methods, an aqueous liquid sample is placed into a sample-receiving chamber in an electrochemical cell that includes two electrodes, e.g., a counter and working electrode. The analyte is allowed to react with a redox reagent to form an oxidizable (or reducible) substance in an amount corresponding to the analyte concentration. The quantity of the oxidizable (or reducible) substance present is then estimated electrochemically and related to the amount of analyte present in the initial sample.

In addition to glucose monitoring, people with diabetes often have to maintain tight control over their lifestyle, so that they are not adversely affected by, for example, irregular food consumption or exercise. In addition, a health care professional (HCP) dealing with a particular person with diabetes may require detailed information on the lifestyle of the individual to provide effective treatment or modification of treatment for managing diabetes. Currently, one of the ways of monitoring the lifestyle of an individual with diabetes has been for the individual to keep a paper logbook of their lifestyle. Another way is for an individual to simply rely on remembering facts about their lifestyle and then relay these details to their HCP on each visit.

The aforementioned methods of recording lifestyle information are inherently difficult, time consuming, and possibly inaccurate. Paper logbooks are not necessarily always carried by an individual and may not be accurately completed when required. Such paper logbooks are small and it is therefore difficult to enter detailed information requiring detailed descriptors of lifestyle events. Furthermore, an individual may often forget key facts about their lifestyle when questioned by a HCP who has to manually review and interpret information from a hand-written notebook. There is no analysis provided by the paper logbook to distill or separate the component information. Also, there are no graphical reductions or summary of the information. Entry of data into a secondary data storage system, such as a database or other electronic system, requires a laborious transcription of information, including lifestyle data, into this secondary data storage. Difficulty of data recordation encourages retrospective entry of pertinent information that results in inaccurate and incomplete records.

Others have attempted to reduce the complexity regarding the operation of the meter by having at least three different user interfaces, as shown in U.S. Pat. No. 7,912,655 to Power et al., ("Power '655"). However, the meter in Power '655 is fixed to these modes without the ability to have the meter customized to the needs of the user based on structured queries.

SUMMARY OF THE DISCLOSURE

Applicants have devised a technique to simplify the selection of the meter's capability but at the same time allow the user to customize the meter's capability to meet the needs of the user in managing diabetes via structured queries presented to the user in order to customize the features in the advanced mode but at the same time preventing any of the features to be used in the basic mode, thereby ensuring simplicity of the meter in the basic mode.

In one aspect, an analyte measurement meter is provided. The meter measures and stores results from analyte measurements and includes a housing, a plurality of user interface buttons proximate the housing, a display proximate the housing; and a microprocessor connected to the user interface buttons and the display. The microprocessor is configured to: (a) allow a user to select a basic mode or advanced mode of the meter with the user interface; (b) upon selection of the advanced mode with the user interface, query the user with a series of inquiries to select any one of at least three features not available in the basic mode; (c) upon selection of any one of the at least three features with the user interface, activation of user-selected feature for the meter; or (d) revert the meter to at least one other feature not available in the basic mode.

In yet another aspect, a method for using an analyte meter is provided. The meter has a microprocessor coupled to a user interface and display. The method can be achieved by: querying a user to select between a basic mode and an advanced mode for the meter; selecting the advanced mode; querying the user for selection for additional features with a series of questions relating to the user's past results, meal patterns, and need for graphical insights; selecting one of the additional features otherwise activating another set of features distinct from the additional features when none of the additional features has been selected; and annunciating a summary of features available in the advanced mode.

Each of the following features can be combined singularly or in combination with each other for use with any of the above aspects. For example, the at least three features may include a glycemic excursion detection functionality that provides for an indication of at least two analyte measurements outside of a predetermined range in a prior number of days (e.g., 3, 4, 5, 6 . . . n days); one of the at least three features may include: a meal-tagging functionality that allows the user to manually or automatically set meal tag before or after a meal; one of the at least three features may include: a graphical display that shows in relation to time of a day information indicative over the prior 7 days of: (a) a number of high analyte measurements; (b) a number of in-range measurements; (c) a number of low analyte measurements; the at least one other feature may include a visual indicator for the display indicative of an analyte measurement with respect to a predetermined range.

These and other embodiments, features and advantages will become apparent to those skilled in the art when taken with reference to the following more detailed description of various exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

MODES FOR CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject invention in a human patient represents a preferred embodiment.

Figure 1:
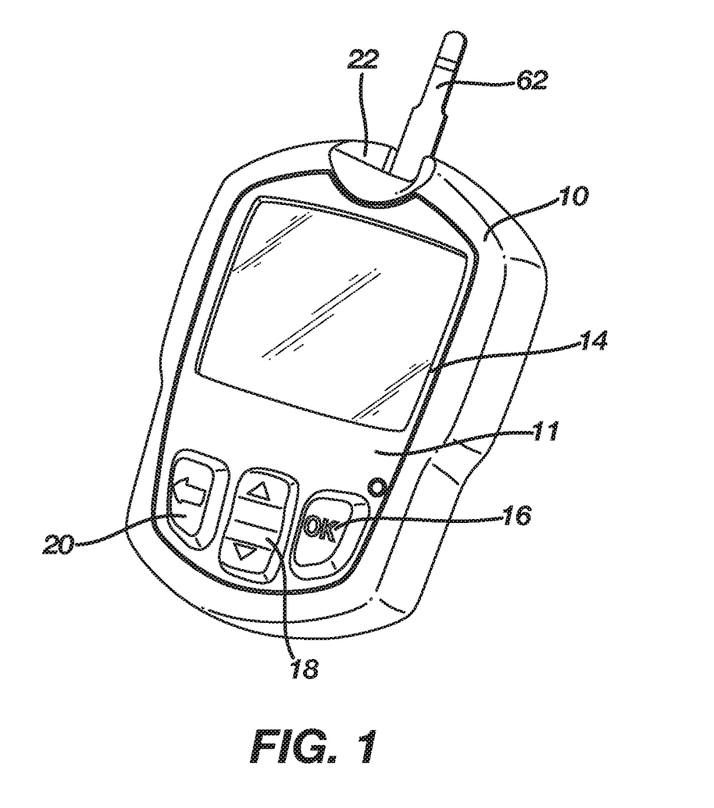
FIG. 1 illustrates a preferred blood glucose measurement system.

FIG. 1 illustrates a diabetes management system that includes a meter 10 and a biosensor in the form of a glucose test strip 62. Note that the meter (meter unit) may be referred to as an analyte measurement and management unit, a glucose meter, a meter, and an analyte measurement device. In an embodiment, the meter unit may be combined with an insulin delivery device, an additional analyte testing device, and a drug delivery device. The meter unit may be connected to a remote computer or remote server via a cable or a suitable wireless technology such as, for example, GSM, CDMA, BlueTooth, WiFi and the like.

Referring back to FIG. 1, glucose meter or meter unit 10 may include a housing 11, user interface buttons (16, 18, and 20), a display 14, and a strip port opening 22. User interface buttons (16, 18, and 20) may be configured to allow the entry of data, navigation of menus, and execution of commands. User interface button 18 may be in the form of a two way toggle switch. Data may include values representative of analyte concentration, or information, which are related to the everyday lifestyle of an individual. Information, which is related to the everyday lifestyle, may include food intake, medication use, occurrence of health check-ups, and general health condition and exercise levels of an individual. The electronic components of meter 10 may be disposed on a circuit board 34 that is within housing 11.

Figure 2:
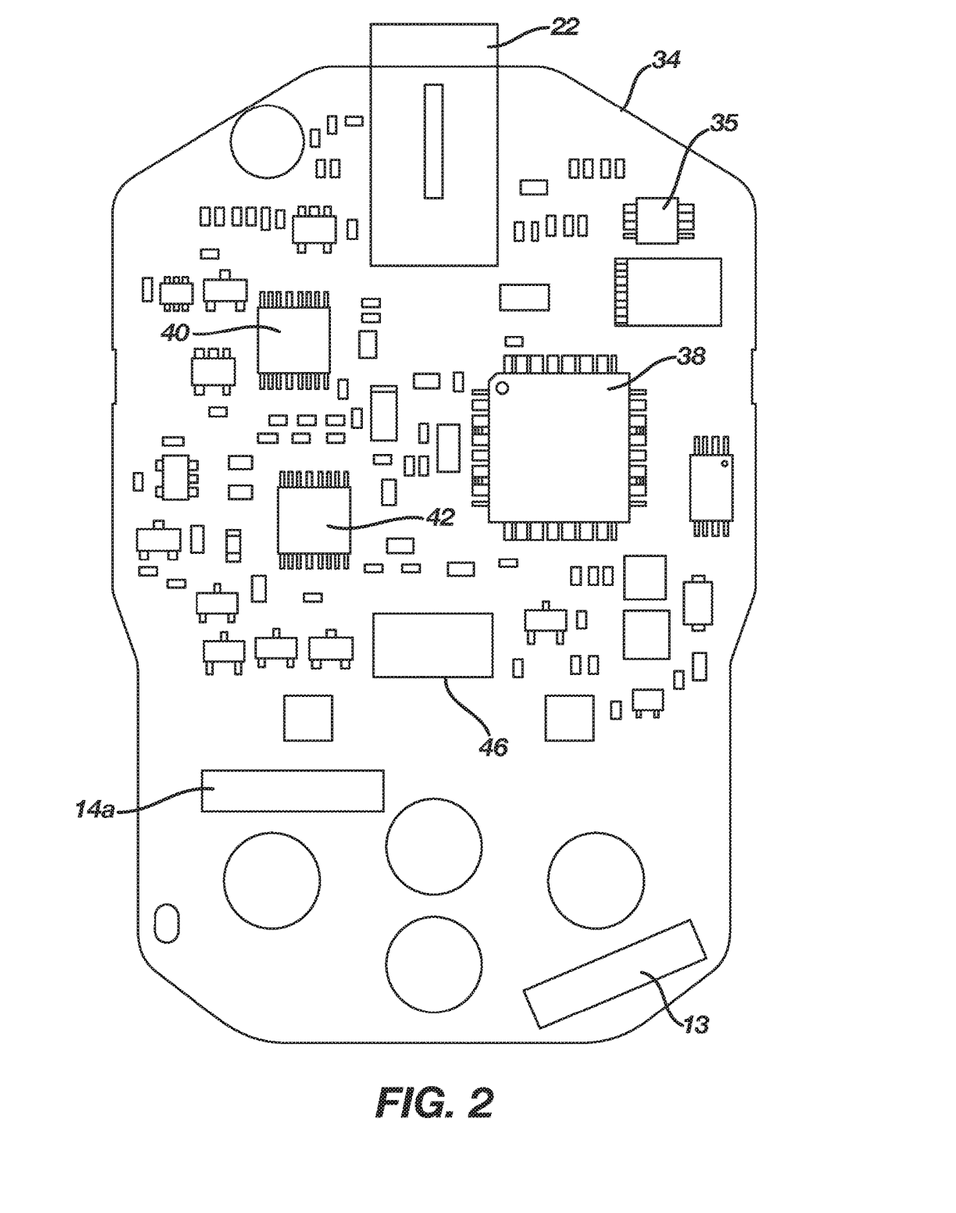
FIG. 2 illustrates the various components disposed in the meter of FIG. 1.

FIG. 2 illustrates (in simplified schematic form) the electronic components disposed on a top surface of circuit board 34. On the top surface, the electronic components include a strip port connector 22, an operational amplifier circuit 35, a microcontroller 38, a display connector 14a, a non-volatile memory 40, a clock 42, and a first wireless module 46. On the bottom surface, the electronic components may include a battery connector (not shown) and a data port 13. Microcontroller 38 may be electrically connected to strip port connector 22, operational amplifier circuit 35, first wireless module 46, display 14, non-volatile memory 40, clock 42, battery, data port 13, and user interface buttons (16, 18, and 20).

Operational amplifier circuit 35 may include two or more operational amplifiers configured to provide a portion of the potentiostat function and the current measurement function. The potentiostat function may refer to the application of a test voltage between at least two electrodes of a test strip. The current function may refer to the measurement of a test current resulting from the applied test voltage. The current measurement may be performed with a current-to-voltage converter. Microcontroller 38 may be in the form of a mixed signal microprocessor (MSP) such as, for example, the Texas Instrument MSP 430. The TI-MSP 430 may be configured to also perform a portion of the potentiostat function and the current measurement function. In addition, the MSP 430 may also include volatile and non-volatile memory. In another embodiment, many of the electronic components may be integrated with the microcontroller in the form of an application specific integrated circuit (ASIC).

Strip port connector 22 may be configured to form an electrical connection to the test strip. Display connector 14a may be configured to attach to display 14. Display 14 may be in the form of a liquid crystal display for reporting measured glucose levels, and for facilitating entry of lifestyle related information. Display 14 may optionally include a backlight. Data port 13 may accept a suitable connector attached to a connecting lead, thereby allowing glucose meter 10 to be linked to an external device such as a personal computer. Data port 13 may be any port that allows for transmission of data such as, for example, a serial, USB, or a parallel port. Clock 42 may be configured to keep current time related to the geographic region in which the user is located and also for measuring time. The meter unit may be configured to be electrically connected to a power supply such as, for example, a battery.

Figure 3:
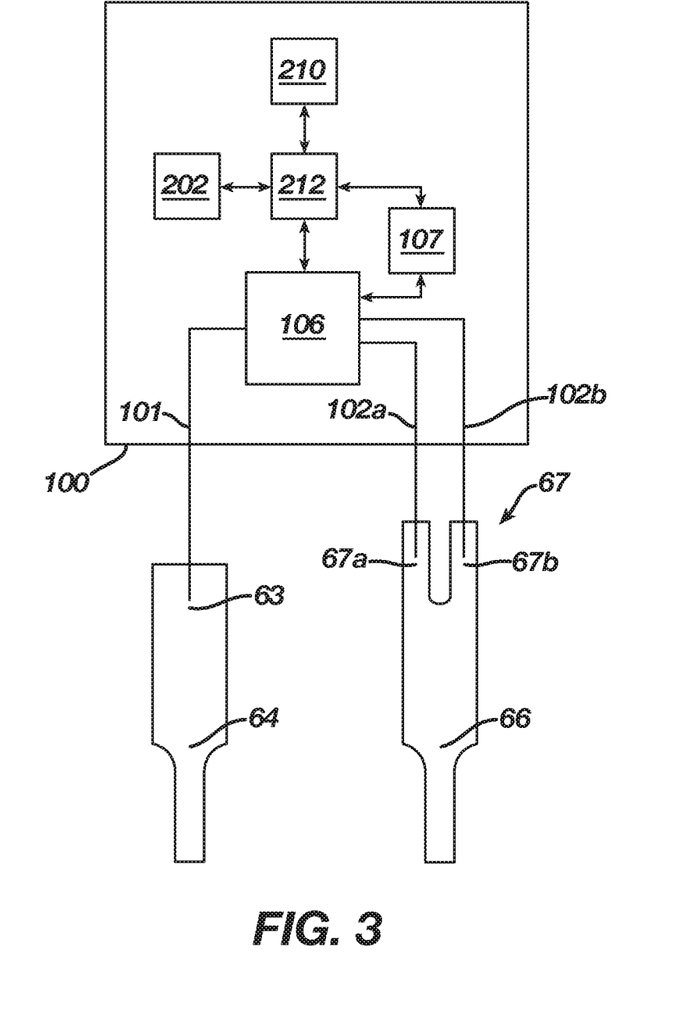
FIG. 3 is a simplified schematic showing a test meter electrically interfacing with portions of a test strip disclosed herein.

FIG. 3 provides a simplified schematic showing a test meter 100 interfacing with a first contact pad 67a, 67b and a second contact pad 63. The second contact pad 63 may be used to establish an electrical connection to the test meter through a U-shaped notch between the two connector prongs 67a and 67b, as illustrated in FIG. 3. In one embodiment, the test meter 100 may include a second electrode connector 101, and first electrode connectors (102a, 102b), a test voltage unit 106, a current measurement unit 107, a processor 212, a memory unit 210, and a visual display 202, as shown in FIG. 3. The first contact pad 67 may include two prongs denoted as 67a and 67b. In one exemplary embodiment, the first electrode connectors 102a and 102b separately connect to prongs 67a and 67b, respectively. The second electrode connector 101 may connect to second contact pad 63. The test meter 100 may measure the resistance or electrical continuity between the prongs 67a and 67b to determine whether the test strip 62 is electrically connected to the test meter 10. The electrodes 64 and 66 here can be utilized to detect physical characteristics of the sample using alternating signals. Alternatively, separate additional electrodes can be provided in the test chamber to allow for detection of the physical characteristics of the sample using alternating signals.

Figure 4:
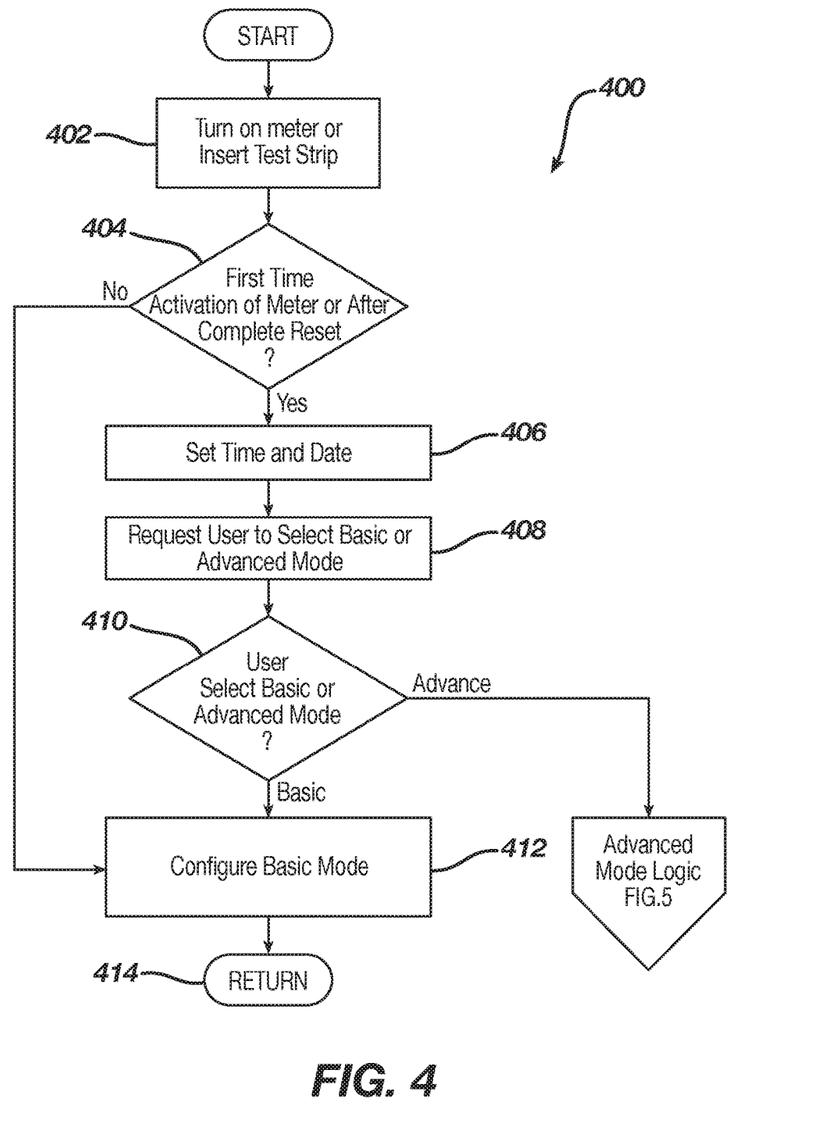
FIG. 4 is an exemplary logic diagram for selection between a basic mode or advanced mode for the meter of FIG. 1.
Figure 5:
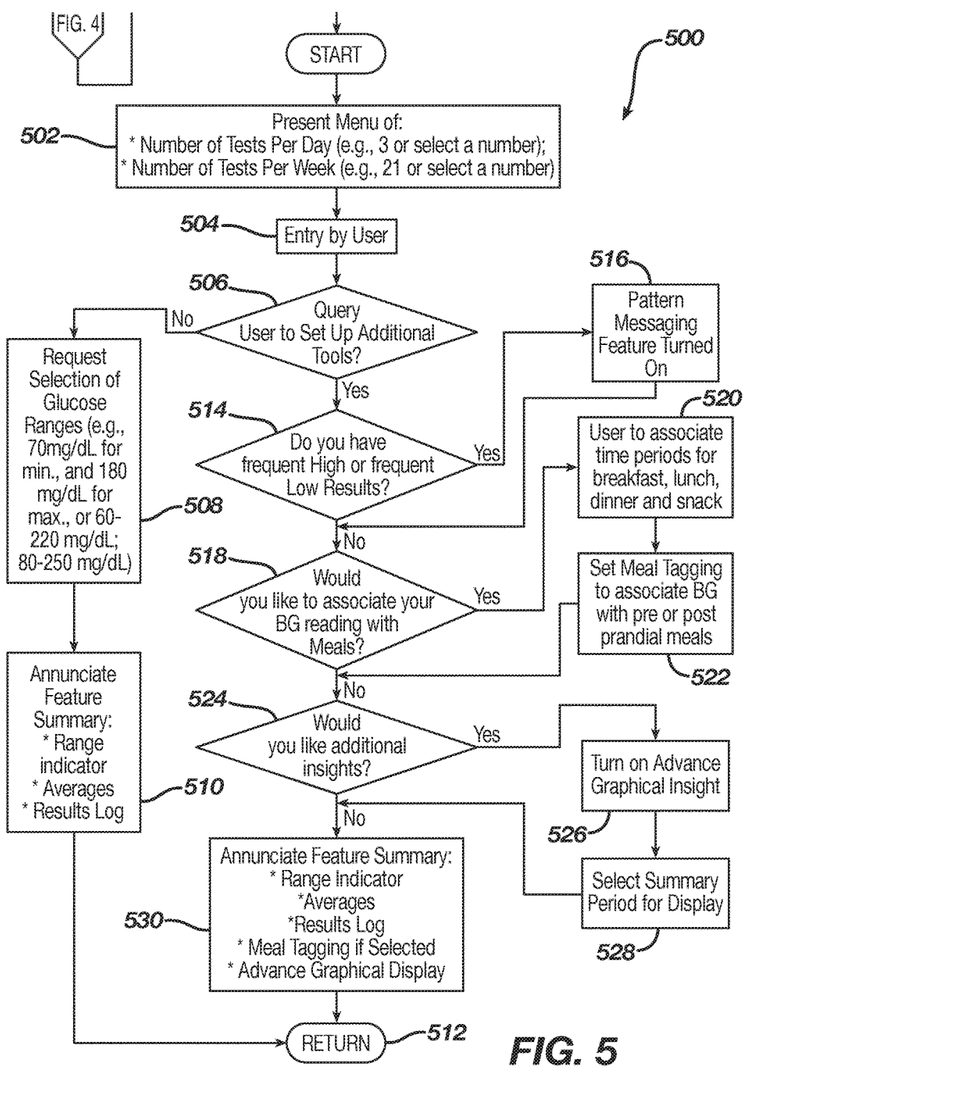
FIG. 5 is an exemplary logic diagram for selection of features in the advanced mode of the meter of FIG. 1.

The meter can be operated in basic or advanced mode as shown in FIGS. 4 and 5. FIG. 4 provides a logic diagram 400 for a user to select between "basic mode" and "advanced mode" starting in step 402 when the meter is turned on. At step 404, the system determines whether this is the first time activation or after a complete reset. If false, the system returns to the main routine at step 414. If true, the logic moves to step 406 to allow the user to set the time and date. At step 408, the system requests the user to select a basic or advanced mode. Upon selection of the basic mode 412, the system configures the meter to provide just the analyte reading (608 in FIG. 6) and whether the result is within a pre-set range of glucose values (610 in FIG. 6). It is noted that the meter is specifically intended to be simple to operate and use in the basic mode. As such, the meter is configured such that no other feature can be added to the meter in the basic mode. In contrast, the meter can be configured to have additional features added to a default mode when in the advanced mode. In other words, the basic mode is locked into its basic features and no other features can be added whereas the advanced mode can be configured to have additional features via structured queries presented to the user. Of course if the user does not desire customization, the meter has a default advanced mode with preset features (step 508).

Referring to FIG. 4, upon selection of the advanced mode, logic 500 would apply, as shown in FIG. 5. In FIG. 5, logic 500 begins with step 502 in which menu is presented to the user to allow the user to indicate how frequently the user tests. As an example, a menu may be presented as a series of questions: "how many times do you test a day?" and "how many times do you test in a week"? After entry by the user at step 504, the system presents another query as to whether the user would like additional tools. If the answer to the query at step 504 is no, the system may use a preset range (e.g., 70 mg/dL to 180 mg/dL) or allow the user to select the range between what are considered to be low analyte and high analyte values for the particular user. At step 510, the system presents or annunciates a summary of the advanced features available on the meter and the system returns to the main routine at step 512. On the other hand, if the user decided to employ additional features which would provide a yes to the query at step 506, the system begins a series of queries to allow the user to customize the advanced features in accordance with the needs of the user.

Specifically, a first query at step 514 is intended for patients who experience routine extremes analyte values over a short period of time but whose average is still within range. For example, a patient who has a 50 mg/dL reading in day one and a 250 mg/dL in day two would have an in-range average of 150 mg/dL. While the average reading of 150 mg/dL may be within range, the physiological effects of the low and high results on the user are not desirable. Hence, for such patient, a high/low pattern detection feature can be turned on at step 516. This functionality determines whether on "X" of the previous "D" days within an "N" hour sliding window of the time of the day of the most recent BG measurement, there has been: (a) a BG measurement above the high threshold (180 mg/dL) or (b) a BG measurement below a low threshold (e.g., 70 mg/dL). If the determination is yes for (a) or (b) or both, a message is provided to the user (e.g., message 630 or 632 in FIG. 6). Details of the high/low pattern detection feature are shown and described in US Patent Application Publication 2011-0205064 filed on Jun. 29, 2010 with the title of "ANALYTE TESTING METHOD AND SYSTEM WITH HIGH AND LOW BLOOD GLUCOSE TRENDS NOTIFICATION", which application is herby incorporated into this application as if fully set forth herein and attached hereto as part of the Appendix. Other structured queries may provide for Meal Tag Averages, assuming that the user has turned on meal tagging from the questionnaire; reminders in case the user needs to test frequently, or customized or pre-programmed such as, for example, After Meal Reminders, Reminder to test 15 minutes after a Low Blood Glucose event.

At step 518, another query allows the selection of manual or automatic meal flagging before or after a meal. The query at step 518 will allow a user to set up for automatic meal flagging by the meter based on the user's habitual meal times at steps 520 and 522. This automatic flagging of analyte results before or after a meal is shown and described in US Patent Application Publication No. 2010-0041084 filed Aug. 12, 2009 , which is hereby incorporated by reference as if fully set forth herein and attached hereto as part of the Appendix. Of course, the user may also set up meal flag to be manual without having the meter select the appropriate flag (pre-meal flag or post-meal flag) as in the case of automatic flagging.

At step 524, another query is provided to allow the user to obtain additional insights as to the user's analyte levels at different times of the day in a graphical format. In the advanced graphical format, information regarding a range of days (e.g., 7, 14, 21, or 30 days) is provided to the user in a table format 626 linking the number of BG results that fall into one of three ranges: (a) low range; (b) within preset (i.e., "in-range") or (c) high with respect to where the BG results occurred in one of the four time periods during the day, which period may be: (1) morning or breakfast; (2) daytime or lunch time; (3) afternoon to evening or dinner; and (4) near bedtime.

Once one or more of the features have been selected via the sequence of structured queries of FIG. 5, the system may annunciate a summary of the advanced features that have been customized for the user at step 538.

To recap, applicants' technique performs the following steps: querying a user to select between a basic mode and an advanced mode for the meter; selecting the advanced mode; querying the user for selection for additional features with a series of questions relating to the user's past results, meal patterns, and need for graphical insights; selecting one of the additional features otherwise activating another set of features distinct from the additional features when none of the additional features have been selected; and annunciating a summary of features available in the advanced mode Consequently, the logic in FIGS. 4 and 5 can be used to operate an analyte meter that measures and stores results from analyte measurements. With the logic programmed into the microprocessor (which is connected to the user interface buttons and the display as is well known), the microprocessor is able to: (a) allow a user to select a basic mode or advanced mode of the meter with the user interface; (b) upon selection of the advanced mode with the user interface, query the user with a series of inquiries to select any one of at least three features not available in the basic mode; (c) upon selection of any one of the at least three features with the user interface, activation of user-selected feature for the meter; or (d) revert the meter to at least one other feature not available in the basic mode.

Applicants note that one of the at least three features may include: (1) glycemic excursion detection functionality that provides for an indication of at least two analyte measurements outside of a predetermined range in a prior number of days (e.g., 3, 4, 5, 6 . . . n days); (2) a meal-tagging functionality that allows the user to manually or automatically set meal tag before or after a meal; or (3) a graphical display that shows in relation to time of a day information indicative over the prior 7 days of (a) a number of high analyte measurements; (b) a number of in-range measurements; (c) a number of low analyte measurements. Also, it is noted that the at least one other feature may include a visual indicator for the display indicative of an analyte measurement with respect to a predetermined range.

Figure 6:
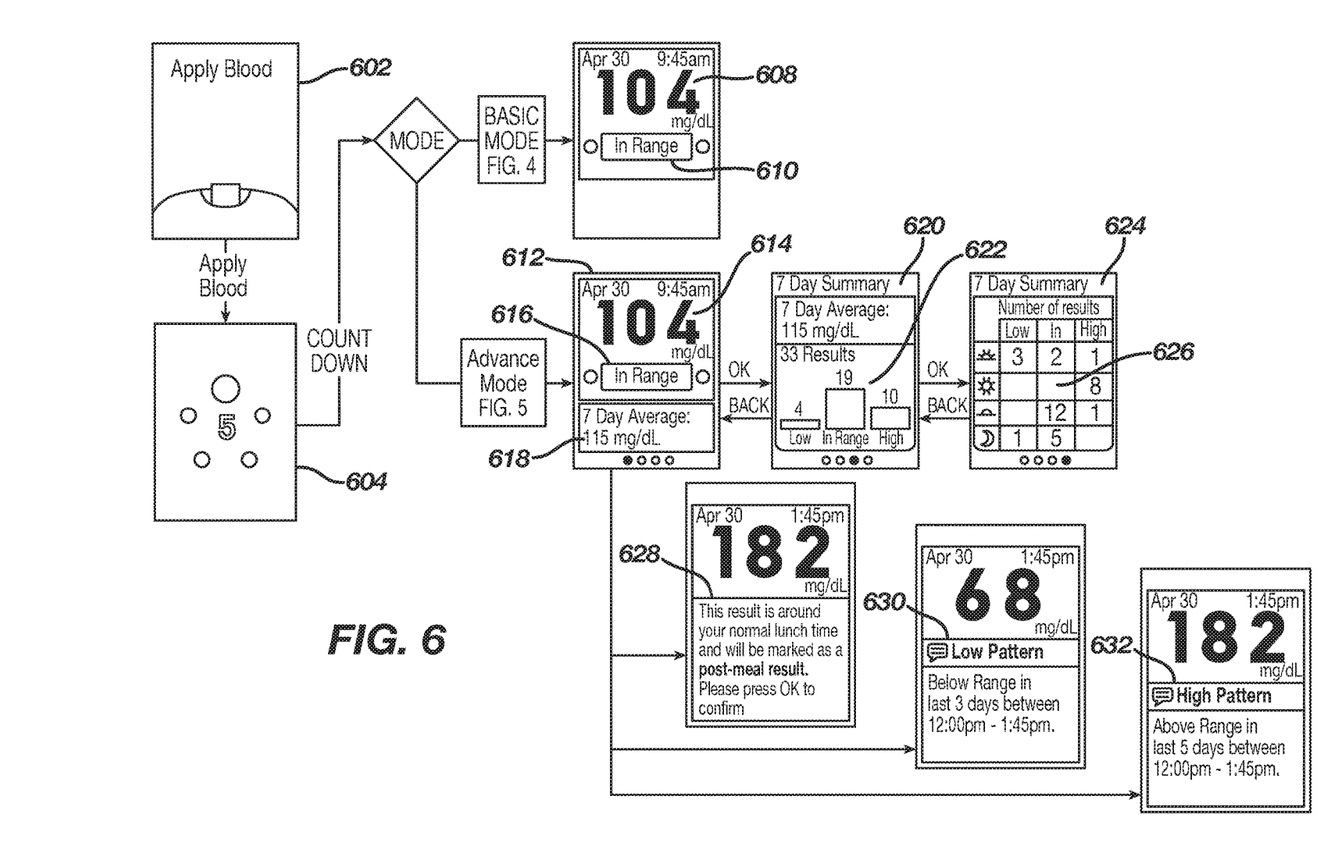
FIG. 6 illustrates a wire frame of various functionalities available in the basic and advanced mode of the meter and exemplary screen shots.

FIG. 6 illustrates an exemplary user's scenario for selection and use of the two modes described earlier in FIGS. 4 and 5. At screen 602, the meter is turned on by insertion of the test strip 62 into the meter. A fluid sample (e.g., blood) is applied to the strip, which activates an analyte measurement sequence. A countdown is initiated in screen 604 and a query is provided at screen 606 to allow the user to select the appropriate mode. Where the basic mode is selected, the meter would provide for an analyte reading (in this case the glucose concentration shown on screen 608) and whether the result within an "in-range" via an indicator on screen 610. On the other hand, if the advanced mode is selected, the structured queries of FIG. 5 (steps 502-538) would apply. Screen shot 612 shows results of the glucose measurement at 614, which is within range at 616, along with the 7-day average at 618. It is noted that screen 612 is that of the advanced mode without any customization made, i.e., a default setup. Depending on the features selected based on the structured queries (FIG. 5), screen 620 can be provided to show not only the average analyte concentration but the total number of results and distribution of the number of the results that are considered to be low, in-range, or high. Screen 624 provides the time-of-the day graphical insight where the number of BG results in the appropriate range (e.g., low, in-range, high) are categorized in these three ranges as well as in the appropriate one of the four periods of the day (morning, day, afternoon, and evening) in graphical layout 626. Furthermore, where the automatic flagging of pre and post meal features is selected, the meter would automatically generate an appropriate flag (post-meal if it appears that the result was taken after the usual meal during such time period of the day) and query the user (message 628) to confirm such automatic flag selection. Similarly, where the high-low pattern detection is turned on, the meter will provide an appropriate message of a low trend pattern 630 occurring in the last 3 days or a high trend pattern 632 occurring in the last 3 days.

Although exemplary embodiments have been shown in relation to these modes, other modes can also be utilized. For example, other modes can be based on individual diagnosis such as gestational diabetes, pediatric diabetes, brittle diabetics where there is a need to maintain blood glucose in a much tighter range, or those with specific co-morbidities (e.g., high blood pressure, cardiovascular complications).

Applicants note that while the exemplary description and figures are to glucose meters and glucose test strips, it is the intention of applicants that the invention is equally applicable to any analyte measurement system, such as, for example, cholesterol, ketone, and similar analytes in physiological fluid such as, for example, sweat, interstitial fluid or blood and the like.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. An analyte measurement meter that measures and stores results from analyte measurements to allow a user to select a basic mode or a configurable advanced mode of the meter with a user interface, the meter comprising:
   a housing;
   a plurality of user interface buttons proximate the housing;
   a display proximate the housing; and
   a microprocessor connected to the user interface buttons and the display, the microprocessor connected to a non-volatile memory stored with logical instructions programmed to cause the microprocessor following powering the meter to:
   upon a first time activation or a reset of the meter, perform mode and feature selection by:
   (a) allowing a user to select between a basic mode and a configurable advanced mode of the meter with the user interface,
   (b) upon selection of the configurable advanced mode with the user interface, querying the user with a series of inquiries, the series of inquiries comprising questions relating to past results of the user, meal patterns of the user, and graphical insights requested by the user,
   (c) receiving from the user, a series of responses corresponding to the series of inquiries, and
   (d) customizing the configurable advanced mode of the meter by applying an advanced mode logic of the meter to the series of responses to the series of inquiries to select any one of at least three features not available in the basic mode, the advanced mode logic comprising a correspondence between the series of responses to the series of inquiries and the at least three features not available in basic mode, wherein the meter is configured to add selected advanced mode features of the at least three features not available in the basic mode to the configurable advanced mode;
   upon any turn-on of the meter subsequent to the first time activation or the reset of the meter and the customizing of the configurable advanced mode, return to a main meter routine without selecting between the basic mode and the advanced configurable mode and using the customized configurable advanced mode to automatically maintain the meter to allow selection and activation of any one of the selected advanced-mode features, and present any one of the selected advanced-mode features to the user with the display; and
   wherein the user interface comprises a first screen and a second screen, the first screen displaying a distribution of analyte concentrations including counts for low, in-range and high analyte concentration measurements, and the second screen comprising a time-of-day distribution of analyte concentrations including counts for low, in-range and high analyte concentration measurements by time-of-day.

2. The meter of claim 1, in which one of the at least three features comprise:

glycemic excursion detection functionality that provides for an indication of at least two analyte measurements outside of a predetermined range in a prior number of days (e.g., 3, 4, 5, 6 . . . n days).

3. The meter of claim 1, in which one of the at least three features comprise:

a meal-tagging functionality that allows the user to manually or automatically set meal tag before or after a meal.

4. The meter of claim 1, in which one of the at least three features comprise a graphical display that shows in relation to time of a day information indicative over the prior 7 days of (a) a number of high analyte measurements; (b) a number of in-range measurements; (c) a number of low analyte measurements.

5. The meter of claim 1, in which the at least one other feature comprises a visual indicator for the display indicative of an analyte measurement with respect to a predetermined range.

\* \* \* \* \*